United States Patent [19]

Rosen et al.

[11] Patent Number: 6,001,340
[45] Date of Patent: *Dec. 14, 1999

[54] **TOPICAL COMPOSITIONS AND METHODS FOR TREATING *PSEUDOFOLLICULITIS BARBAE* AND INGROWN HAIR**

[75] Inventors: Steven E. Rosen, 2150 SW. 90th Ave., Unit "A", Ft. Lauderdale, Fla. 33324; Robert Lee Brown, Irving, Tex.

[73] Assignee: Steven E. Rosen, Ft. Lauderdale, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/039,843

[22] Filed: Mar. 30, 1993

[51] Int. Cl.⁶ .................................................... A61K 7/15
[52] U.S. Cl. .............................. 424/73; 424/60; 514/165; 514/513
[58] Field of Search ........................ 424/73, 60; 514/513, 514/165

[56] References Cited

U.S. PATENT DOCUMENTS

| | | | |
|---|---|---|---|
| 3,136,696 | 6/1964 | Harrison et al. | 424/73 |
| 4,199,576 | 4/1980 | Reller et al. | 514/159 |
| 4,946,710 | 8/1990 | Partain, III et al. | 514/777 |
| 5,034,221 | 7/1991 | Rosen et al. | 424/73 |
| 5,204,093 | 4/1993 | Victor | 424/73 |
| 5,223,267 | 6/1993 | Nichols | 424/489 |

*Primary Examiner*—Neil S. Levy
*Attorney, Agent, or Firm*—Needle & Rosenberg, P.C.

[57] ABSTRACT

Topical compositions and methods are disclosed for the treatment of pseudofolliculitis barbae and ingrown hair. The compositions comprise acetylsalicylic acid, propylene glycol, glycerine, and isopropyl alcohol. The method involves the step of applying the composition to the beard areas of the face after shaving. The acetylsalicylic acid is dissolved in a solvent mixture comprising propylene glycol, glycerine, and isopropyl alcohol. The acetylsalicylic acid is present in the range of between about 5 percent by weight per unit volume of the solvent mixture up to saturation of the solvent mixture. The solvent mixture comprises propylene glycol in the range of about 5 to 15 percent by volume, glycerine in the range of about 1 to 10 percent by volume, and the balance of the volume made up with isopropyl alcohol alone or a solution comprising at least 50 percent by volume of isopropyl alcohol. The isopropyl alcohol can be in a solution with water, methanol, or ethanol, provided that the polarity of the resulting solution is not so high that the acetylsalicylic acid would readily precipitate from the solution at ordinary room temperature ranges.

4 Claims, No Drawings

TOPICAL COMPOSITIONS AND METHODS FOR TREATING *PSEUDOFOLLICULITIS BARBAE* AND INGROWN HAIR

BACKGROUND OF THE INVENTION

The present inventions relate to improvements in topical compositions and methods for the treatment and prevention of pseudofolliculitis barbae and ingrown hair.

Pseudofolliculitis barbae is the clinical name given to the condition commonly known as "razor bumps." Generally, this condition is described as the ingrowth of emerged hairs back into the skin at a location adjacent to the follicle from which the hair has emerged. This penetration back into the skin causes an antigenic foreign body reaction at the point of penetration, resulting in lesions consisting of firm papules and pustules in which the ingrown hair can become buried. Infections can become superimposed upon this basic state, augmenting the inflammatory reaction. Thus, further shaving becomes difficult and painful.

Pseudofolliculitis barbae is caused by shaving strong and highly curved hairs. For this reason, the condition tends to have a greater incidence in the bearded areas of males of the Negro race. However, it also affects other races, and ingrown hairs can be a problem for other shaved areas such as the underarms and legs. These curved hairs, instead of emerging straight from the hair follicle and the surface of the skin, tend to emerge oriented parallel to the skin surface and, owing to their curvature, are mechanically biased toward reentry into the skin. Because these hairs are curved, they often are not closely cut at their point of emergence during shaving. In practice, shaving serves to obliquely cut the biased hair rather than cut across the cross-section of the hair, leaving a relatively sharp point at the tips that facilitates skin penetration. Before the next shave, the point or tip of the hair grows into the skin, bringing about the reaction and condition of pseudofolliculitis barbae.

As may be appreciated, total abstinence from shaving is not, for the most part, a practical solution to the problem. Short of abstinence from shaving, however, prevention of pseudofolliculitis barbae has proven difficult. In theory, frequent shaving to cut emerging hairs closer to the skin surface should eliminate the condition by regularly removing the hairs before they grow and re-enter the skin. In practice, however, shaving frequently enough and close enough to skin level to avoid the condition is difficult.

Some efforts to cut facial hair at the skin level have involved stretching the skin, which actually results in the cutting of the hairs below the skin level. This can result in an intra-follicular ingrown hair in which the sharp tip of the curved hair, instead of emerging from the follicle, penetrates the follicle wall to bring about the same or similar foreign body reaction as would occur when a hair normally emerges from the follicle but then re-enters the skin.

The use of depilatory compositions has been suggested for the prevention of pseudofolliculitis barbae and ingrown hair. For some persons, this can be effective in achieving the non-cutting removal of the hairs before they can re-enter the skin. However, for others, the depilatory itself can be an irritant and cause a dermatological reaction. Also suggested have been compositions that soften the facial hair to inhibit their ability to penetrate the skin. However, most of these compositions bring about skin irritations or other dermatological side effects when used with the necessary frequency to present a regularly clean-shaven appearance.

Prior art known to the inventors concerning the subject of pseudofolliculitis barbae includes the following references: U.S. Pat. No. 3,981,681 issued to Mario de la Guarida on Sep. 21, 1976; U.S. Pat. No. 4,228,163 issued to William E. Bliss on Oct. 14, 1980; U.S. Pat. No. 4,525,344 issued to Ronald J. Tutsky on Jun. 25, 1985; U.S. Pat. No. 4,775,530 issued to Nicholas V. Perricone on Oct. 4, 1988; and U.S. Pat. No. 5,034,221 issued to Steven E. Rosen et al. on Jul. 23, 1991. In particular, U.S. Pat. No. 5,034,221 (the '221 patent) discloses a treatment for pseudofolliculitis barbae involving the topical application to the beard areas of the face a composition consisting essentially of acetylsalicylic acid, corn starch, isopropyl alcohol, and aloe vera. The '221 patent teaches the advantages of the composition including corn starch and aloe vera gel. Although the invention disclosed in the '221 patent is helpful in the treatment of the condition, improvements and different advantages are desirable in the treatment of pseudofolliculitis barbae.

Also known to the inventors herein are U.S. Pat. No. 4,219,548 issued to Herbert H. Reller on Aug. 26, 1980; U.S. Pat. No. 4,364,940 issued to Edward S. Neiss et al. on Dec. 21, 1982; and U.S. Pat. No. 4,665,063 issued to Daniel Bar-Shalom on May 12, 1987. These references are nonanalogous to the present invention because they primarily relate to the treatment of acne. It may be appreciated that the cause and nature of acne differs materially from pseudofolliculitis barbae and ingrown hair. Acne is an inflammatory condition involving the sebaceous or oil glands of the skin, most commonly the skin of the face. The causes and condition of acne are unrelated to the causes and condition of pseudofolliculitis barbae and ingrown hair.

U.S. Pat. No. 4,665,063 (the Bar-Shalom patent) also relates to the treatment of psoriasis and seborrhea. Although the causes of these noninfectious dermatological disorders are not known to the inventors, psoriasis and seborrhea are both characterized by crusting and flaking lesions of the skin, which symptoms do not occur in infectious pseudofolliculitis barbae. Furthermore, psoriasis and seborrhea commonly affect skin other than that of the face. Thus, it appears that whatever the causes of these other conditions, they are totally unrelated to the known causes of pseudofolliculitis barbae and ingrown hair.

The Bar-Shalom patent suggests in general terms the use of acetylsalicylic acid at a concentration of at least 11% by weight in a suitable "carrier" for the treatment of dermatological disorders such as acne, psoriasis, and seborrhea. Furthermore, the patent states that "[w]hile physiologically acceptable and compatible carriers for the acetyl salicylic acid include liquid paraffin, lanolin, white soft paraffin, white bees wax and certain alcohols such as propanol, isopropyl alcohol, glycerol and glycol, along with mixtures of any thereof, the especially-preferred carrier for the acetyl salicylic acid is ethanol alone, with the acetyl salicylic acid being present in the ethanol in the amount of 11% by weight to saturation" (which is about 12.5–13% by weight in ethanol). Thus, the Bar-Shalom patent suggests that other than the especially-preferred carrier of ethanol alone, any one or more of the multitude of listed carriers is acceptable and combinations of such carriers may be used in any proportions. Several of these ingredients are unsuitable for the treatment of pseudofolliculitis barbae and ingrown hair and are irritating to the delicate facial skin, particularly at high concentrations, however, the Bar-Shalom patent makes no distinction among them.

SUMMARY OF THE INVENTIONS

Improved compositions particularly adapted for the treatment and prevention of pseudofolliculitis barbae and ingrown hair have been discovered, the compositions comprising acetylsalicylic acid, propylene glycol, glycerine, and isopropyl alcohol. The acetylsalicylic acid is a solid organic chemical compound that is dissolved in a solvent mixture comprising propylene glycol, glycerine, and isopropyl alcohol.

The acetylsalicylic acid is present in the range between about 5 percent by weight per unit volume of the solvent mixture up to saturation of the solvent mixture.

The solvent mixture comprises propylene glycol in the range of about 5 to 15 percent by volume, glycerine in the range of about 1 to 10 percent by volume, and the balance of the volume made up with isopropyl alcohol alone or a solution comprising at least 50 percent by volume of isopropyl alcohol. The isopropyl alcohol can be in a solution with water, methanol, or ethanol, for example, provided that the polarity of the resulting solution is not so high that the acetylsalicylic acid would readily precipitate from the solution at ordinary room temperature ranges.

It has been discovered that the combination of these substances in these proportion ranges produce unexpected improvements and advantages over the prior art treatments for pseudofolliculitis barbae and ingrown hair.

The improved compositions can include, if desired, effective amounts of other ingredients such as coloring agents, fragrance, and medications to further soothe and aid in healing the condition.

The method of treating pseudofolliculitis barbae and ingrown hair comprises the steps of shaving the beard areas or other areas of the skin, applying to the affected area of the skin an effective amount of one of the previously described compositions, and preferably allowing at least some of the isopropyl alcohol to evaporate before pat drying with a dry towel. For best results the composition should not be immediately washed off or otherwise removed. In severe cases, the composition can be applied at least once sometime between shavings, for example at night before retiring to bed.

It is an object of the invention to provide an improved product and method for the treatment of pseudofolliculitis barbae and ingrown hair that can be employed without the occurrence of skin irritation or other harmful side effects. These and other objects and advantages of the invention will become apparent to those skilled in the art upon reading the following detailed description of preferred embodiments.

DETAILED DESCRIPTION OF PREFERRED EMBODIMENTS

It has been determined that compositions consisting essentially of acetylsalicylic acid, propylene glycol, glycerin, and isopropyl alcohol can be highly effective in the treatment and prevention of pseudofolliculitis barbae and ingrown hair. The acetylsalicylic acid is present in the range of between about 5 percent by weight per unit volume of the solvent mixture up to saturation of the solvent mixture. The solvent mixture comprises propylene glycol in the range of about 5 to 15 percent by volume, glycerine in the range of about 1 to 10 percent by volume, and the balance of the volume substantially made up with isopropyl alcohol alone or a solution comprising at least 50 percent of isopropyl alcohol. For example, the isopropyl alcohol can be in a solution with water, methanol, or ethanol, provided that the polarity of the resulting composition is not so high that the acetylsalicylic acid would readily precipitate from solution at ordinary room temperatures. More preferably, the acetylsalicylic acid should not precipitate at temperatures above about 50° F.

In more preferred embodiments of the invention, the acetylsalicylic acid preferably is present in the range of about 10 percent by weight per unit volume of the solvent mixture up to saturation of the solvent mixture. Furthermore, the propylene glycol preferably is present in the solvent mixture in the range of about 10 to 15 percent by volume. The glycerine is preferably present in the solvent mixture in the range of about 2 to 4 percent by volume. And the balance of the solvent mixture preferably is substantially made up with isopropyl alcohol alone or a solution of isopropyl alcohol and water, provided that the isopropyl alcohol is at least about 70 percent by volume of the solution of isopropyl alcohol and water.

In a most preferred embodiment of the invention, which appears to be the most effective and soothing to the skin, the acetylsalicylic acid is present in the range of about 15 percent by weight per unit volume of the solvent mixture up to saturation of the solvent mixture and the solvent mixture comprises propylene glycol in about 10 percent by volume, glycerine in about 2 percent by volume, and the balance of the volume substantially made up with isopropyl alcohol alone or a solution of isopropyl alcohol and water, provided that the isopropyl alcohol is at least about 70 percent by volume of the solution of isopropyl alcohol and water. Where the isopropyl alcohol is about 70 percent by volume of the solution of isopropyl alcohol and water, the saturation concentration of the acetylsalicylic acid in this solvent mixture is about 18 percent by weight per unit volume.

These formulations have been empirically tested on a limited basis with a few persons and the results have been most positive, particularly for the presently most preferred embodiment of the invention. Although the inventors do not purport to know why the new compositions are effective, it is believed that the acetylsalicylic acid (aspirin) is important for softening the hair and reducing the degree of curvature in the hair. Thus, the treated hair has neither the mechanical strength nor the high degree of curvature necessary to penetrate the skin or follicle wall, thereby reducing or eliminating the basic cause of pseudofolliculitis barbae and ingrown hair.

Propylene glycol (1,2-propanediol; methylene glycol) appears to be an important solvent carrier for the acetylsalicylic acid. Furthermore, it is a moisturizer and produces a pleasant emollient feel when applied to the skin. Propylene glycol has the additional benefit of being a mild germicide, which helps reduce the likelihood of infection. However, in excessive concentrations the germicidal properties can irritate sensitive facial skin. The inventors are not aware of an effective equivalent to propylene glycol and believe it is critical to the effectiveness of the composition.

Glycerine (glycerol; 1,2,3-propanetriol) is a mild astringent that causes increased blood flow to the skid and allows the propylene glycol to carry the acetylsalicylic acid into the epidermis and hair follicles. Excessive amounts of glycerine could allow the propylene glycol to penetrate below the epidermis, which would be undesirable for the most effective treatment of pseudofolliculitis barbae and ingrown hair. The inventors are not aware of an effective equivalent to glycerine and believe it is critical to the effectiveness of the composition.

Isopropyl alcohol (isopropanol; 2-propanol) or a solution of isopropyl alcohol and water serves as a bulk solvent for applying the other ingredients of the composition to the beard areas of the face. Isopropyl alcohol also serves to dissolve oils and grease thus cleaning the skin and permitting more intimate contact of the other ingredients with the skin. Isopropyl alcohol is less drying than ethanol, and because it is less polar, it is a better solvent for the acetylsalicylic acid. The inventors are not aware of an effective equivalent to isopropyl alcohol and believe it also is critical to the effectiveness of the composition It is anticipated, however, that some ethanol in the composition would not adversely effect the effectiveness the composition.

Acetylsalicylic acid, propylene glycol, glycerin, and isopropyl alcohol are all generally recognized as safe for topical application to the skin or for cosmetic purposes.

In preparing the composition it can be helpful to gently warm the solvent mixture of propylene glycol, glycerine, isopropyl alcohol, and water (if any) to assist the acetylsalicylic acid in completely dissolving in the solvent It has been observed that the typical consumer tends to prefer a product that is homogeneous in appearance and without any precipitate. The acetylsalicylic acid is virtually insoluble in water or water based substances. Thus, aloe vera, for example, while it is soothing to the skin, does not deliver as much of the acetylsalicylic acid in solution to the skin but rather tends to hold it in suspension away from the skin.

In a presently most preferred embodiment, an effective amount of a coloring agent such as FD&C Blue No. 6 is added to the composition to effect a pleasing blue color to the product. Furthermore, fragrance such as citrus is also added to create a pleasant smell. A pleasing fragrance can persist after the application of the solution to the face in the manner of a cologne.

The preferred method includes the steps of first thoroughly washing the face with soap and water to remove oil and dirt particles from the skin, shaving the beard areas using whatever method is preferred, and rinsing and drying the face. The composition is then evenly applied to the beard areas of the face with the fingers and hands. The isopropyl alcohol is allowed to evaporate for a few moments before pat drying with a towel, which leaves the other ingredients evenly applied to the skin. For best results the composition should not be immediately washed off or otherwise removed.

The examples described above are only exemplary. Even though numerous characteristics and advantages of the present inventions have been set forth in the foregoing description, together with our understanding of the function of the components, the disclosure is illustrative only, and changes may be made in the composition within the principles of the inventions to the full extent indicated by the broad general meaning of the terms used in the attached claims. The limits of the inventions and the bounds of the patent protection are measured by and defined in the following claims.

Having described the inventions, what is claimed is:

1. A composition for the treatment of pseudofolliculitis barbae and ingrown hair consisting essentially of:

acetylsalicylic acid in the range of about 10 to 18 percent by weight per unit volume of a solvent mixture, said solvent mixture consisting essentially of:

propylene glycol in the range of about 10 to 15 percent by volume, glycerine in the range of about 2 to 4 percent by volume, and the balance of said solvent mixture made up with a solution of isopropyl alcohol and water, wherein said solution of isopropyl alcohol and water is at least 70 percent by volume isopropyl alcohol.

2. A composition for the treatment of pseudofolliculitis barbae and ingrown hair that is homogeneous in appearance, said composition consisting essentially of:

(a) acetylsalicylic acid in the range of about 10 to 18 percent by weight per unit volume of a solvent mixture; and (b) said solvent mixture consisting essentially of:
   (i) propylene glycol in the range of about 10 to 15 percent by volume,
   (ii) glycerin in the range of about 2 to 4 percent by volume,
   (iii) a solution of isopropyl alcohol, ethanol and water, wherein said solution is at least 70 percent by volume isopropyl alcohol and further wherein the acetylsalicylic acid does not precipitate out of the solvent mixture at ambient temperature or above.

3. The composition according to claim 2 wherein the acetylsalicylic acid does not precipitate out at 50° F. or above.

4. A homogenous topical composition for the treatment of psuedofolliculitas barbae comprising:

(a) acetylsalicylic acid, present in an amount of about 5–18% by weight of the composition; and (b) a solvent mixture comprising:
   (i) propylene glycol, present in an amount of about 5–17% by weight of the composition;
   (ii) glycerine, present in an amount of about 1–14% by weight of the composition;
   (iii) isopropyl alcohol, present in an amount not less than about 27 %by weight of the composition;
   (iv) ethanol, present in an amount of 0–32% by weight of the composition; and
   (v) water;

wherein the acetylsalicylic acid is completely dissolved in the solvent mixture at ambient temperature.

* * * * *

UNITED STATES PATENT AND TRADEMARK OFFICE
CERTIFICATE OF CORRECTION

PATENT NO. : 6,001,340
DATED : December 14, 1999
INVENTOR(S) : Steven E. Rosen and Robert Lee Brown It is certified that error appears in the above-identified patent and that said Letters Patent is hereby corrected as shown below:

<u>Title page,</u>
Item [75], Inventors, add -- James Agard --.

Signed and Sealed this

Thirtieth Day of May, 2006

JON W. DUDAS
*Director of the United States Patent and Trademark Office*